United States Patent [19]
Erickson et al.

[11] Patent Number: 5,499,917
[45] Date of Patent: Mar. 19, 1996

[54] DENTAL ISOLATION DAM

[75] Inventors: Robert L. Erickson, Woodbury; Paul E. Hansen, Lake Elmo; Paul A. Burgio, White Bear Lake; Joel D. Oxman, St. Louis Park; James D. Christoff, Birchwood, all of Minn.

[73] Assignee: Minnesota Mining and Manufacturing Company, St. Paul, Minn.

[21] Appl. No.: 355,808

[22] Filed: Dec. 14, 1994

Related U.S. Application Data

[63] Continuation of Ser. No. 84,529, Jun. 29, 1993, abandoned.

[51] Int. Cl.$^6$ ..................................................... A61C 5/14
[52] U.S. Cl. .......................................... 433/137; 433/138
[58] Field of Search .................................. 433/136, 137, 433/138; 128/850, 851, 852, 853, 854, 855

[56] References Cited

U.S. PATENT DOCUMENTS

| | | | |
|---|---|---|---|
| Re. 31,285 | 6/1983 | van Turnhout et al. | 55/155 |
| 1,292,095 | 1/1919 | Schwartz . | |
| 2,081,779 | 5/1937 | Titus | 433/137 |
| 3,575,782 | 4/1971 | Hansen | 161/141 |
| 4,195,629 | 4/1980 | Halford | 128/206.13 |
| 4,215,682 | 8/1980 | Kubik et al. | 128/205.29 |
| 4,233,025 | 11/1980 | Larson et al. | 433/136 |
| 4,259,067 | 3/1981 | Nelson | 433/93 |
| 4,499,896 | 2/1985 | Heinecke | 128/156 |
| 4,552,795 | 11/1985 | Hansen et al. | 428/110 |
| 4,626,211 | 12/1986 | Coston | 433/137 |
| 4,640,859 | 2/1987 | Hansen et al. | 428/105 |
| 4,721,465 | 1/1988 | Barasz | 433/137 |
| 4,828,491 | 5/1989 | Gray | 433/136 |
| 4,871,311 | 10/1989 | Hagne | 433/136 |
| 4,969,473 | 11/1990 | Bothwell | 433/136 |
| 4,984,584 | 1/1991 | Hansen et al. | 128/898 |
| 5,011,409 | 4/1991 | Gray | 433/136 |
| 5,104,317 | 4/1992 | Rizai | 433/136 |
| 5,152,686 | 10/1992 | Duggan et al. | 433/93 |
| 5,226,815 | 7/1993 | Bowman | 433/137 |

FOREIGN PATENT DOCUMENTS 2232084  5/1990  United Kingdom .

OTHER PUBLICATIONS

Brochure, "Hygenic Dental Dam and Application Accessories", The Hygenic Corporation, Akron, Ohio, Copyright 1990.

Brochure, "There are millions of reasons to use dental dam routinely", The Hygenic Corporation, Akron, Ohio, Copyright 1993.

M. A. Cochran, C. H. Miller, M. A. Sheldrake, "The efficacy of the rubber dam as a barrier to the spread of microorganisms during dental treatment", *JADA*, vol. 119, Jul. 1989, pp. 141–144.

Advertisement for Quickdam Isolation Device by Ivoclar Vivadent, *Dental Products Report*, Feb. 1993, p. 49.

M. A. Champion, G. Kugel, C. Gruskowski, "Evaluation of a New Intraoral Isolation Device", *Operative Dentistry*, 1991, 16, 181–185.

*Primary Examiner*—Cary E. O'Connor
*Attorney, Agent, or Firm*—Gary L. Griswold; Walter N. Kim; James D. Christoff

[57] ABSTRACT

A dental isolation dam has a plurality of elastic fibers arranged in a rectangular, crisscrossed pattern between impervious films. The fibers enable the dam to be easily placed, and, once released, clinch around necks of isolated teeth to provide enhanced moisture and infection control.

37 Claims, 2 Drawing Sheets

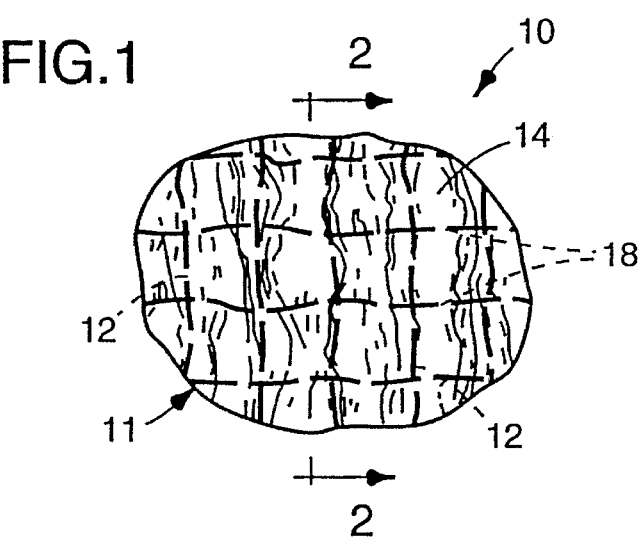
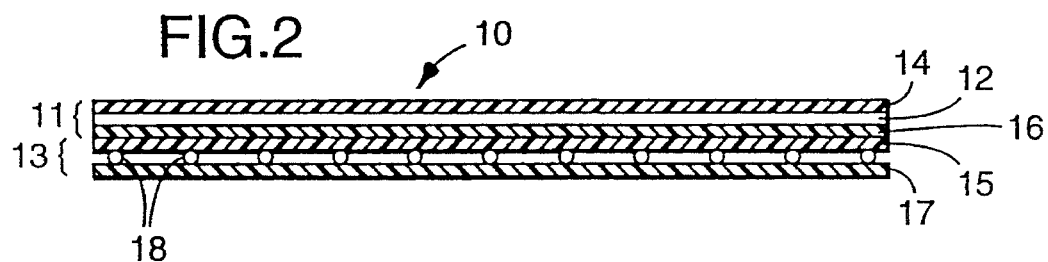
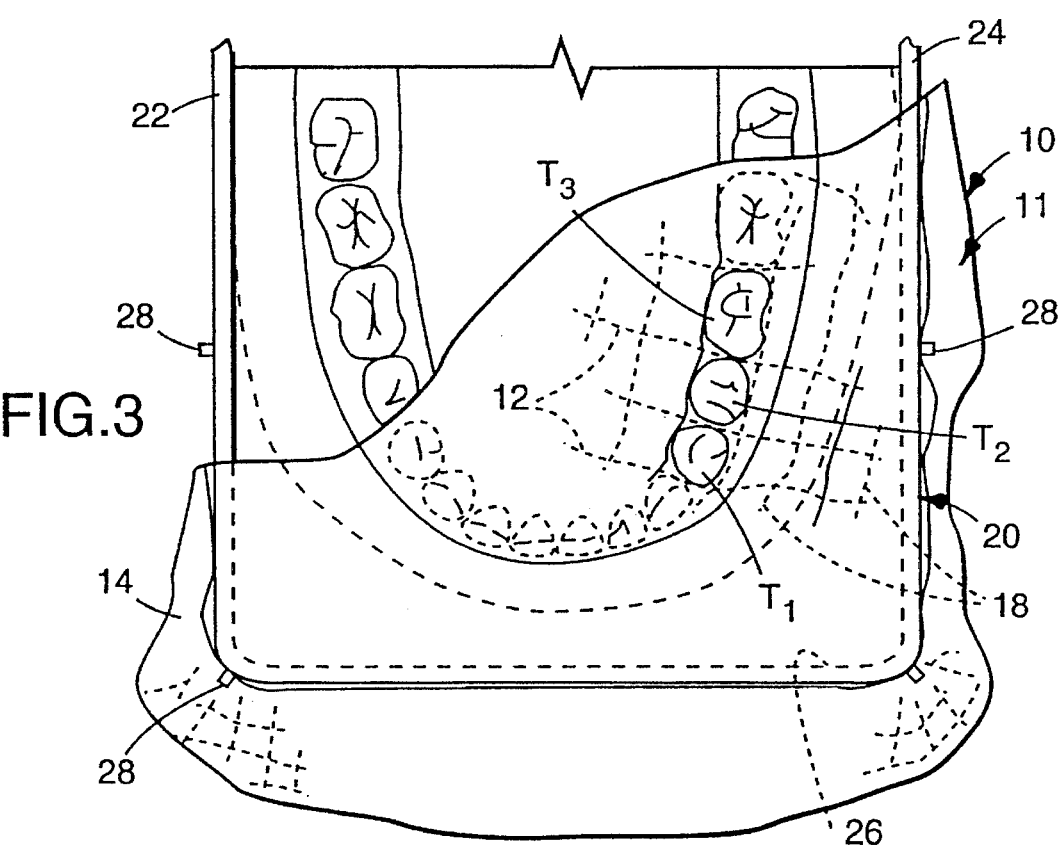

DENTAL ISOLATION DAM

This is a continuation of application Ser. No. 08/084,529, filed Jun. 29, 1993, now abandoned.

BACKGROUND OF THE INVENTION

1. Field of the Invention

This invention relates to a dental dam for isolation, moisture control and infection control in the oral environment.

2. Description of the Related Dental Art

Dental isolation dams are commercially available for use in dental procedures where maintenance of a dry working area and containment of contaminants is desirable. Two known dams include "Dental Dam" (from The Hygenic Corp., Akron, Ohio) and "Quickdam" (from Ivoclar North America Vivadent Division, Amhurst, N.Y.). Dental dams are commonly made of natural rubber and referred to as rubber dams. Dental dams are typically available in discrete sheets, rolls and preformed ovals and are sometimes used with a separate metal frame to assist in retaining the dam in a desired configuration.

Prior to use, the dam is typically perforated with a punch at a location corresponding with the position of the tooth to be isolated. The dam is then placed in the mouth with the perforation positioned over the tooth and moved until the tooth projects through the perforation. The dam is typically clamped with a retention clamp to an adjacent tooth to maintain the desired placement and in some instances is secured about the neck of the tooth with a cord such as dental floss. Next, the dam is stretched over a frame to keep it taut.

U.S. Pat. No. 5,104,317 discloses a dam maintained in place utilizing a separate elastomeric cord. Great Britain Patent Application No. 2 232 084A describes a dental dam with an aspirator frame having hollow pipes fitted to a central exhaust for suctioning fluids in the oral cavity. An attempt to provide a dental dam that needs no separate external frame is disclosed in U.S. Pat. No. 4,828,491 which describes an oval-shaped dam having an attached annular resilient frame.

It has been proposed to make dental dams of polyurethanes as described in U.S. Pat. No. 4,828,491. The dam illustrated in one embodiment of U.S. Pat. No. 4,828,491 has a series of ribs arranged along a radial axis perpendicular to and adjacent a peripheral annular rim such that the ribs coincide with the location of interproximal areas of the dental arch.

The dental dam is increasingly recommended for use as part of the infection control armamentarium for standard dental procedures. However, dams are relatively infrequently used because they are often cumbersome for the dental practitioner to place, difficult to maintain in position and uncomfortable for the patient. An easy to place dam with need for little or no attendant hardware and providing comfort for the patient would be a significant inducement for dental dams to be utilized more frequently during standard operatory procedures.

OTHER ART

U.S. Pat. Nos. 4,552,795 and 4,640,859 describe a web made of a heat-elasticized, flat, inelastic sheet material for utilization in disposable diapers. U.S. Pat. Nos. 3,575,782 and 4,984,584 describe laminate materials with two fibrous webs having partially extended spaced aligned elastic yarns sealed therebetween for use in elastic bandages.

SUMMARY OF THE INVENTION

The present invention in one embodiment is directed toward a dental isolation dam comprising a first film and a second film, wherein at least a portion of one of the films is impervious. The dam also includes a first set of elastic fibers extending in generally parallel directions and located between the first film and the second film. At least certain fibers of the first set of fibers are arranged in adjacent pairs and are spaced apart a distance generally equal to the average mesial-distal width of a tooth.

In another embodiment of the invention, a dental isolation dam comprises an impervious film, and a mask portion for covering the nose. The mask portion is connected to the film and includes a section of filtration material.

The invention also is directed to a dental procedure that comprises the steps of placing a dental dam over at least a portion of the oral cavity of a patient, moving the dam to cause at least one tooth to project through a hole in the dam, and adhesively connecting a portion of the dam to the patient to facilitate retaining the dam in place.

The present invention also concerns a dental isolation dam comprising a first film and a second film, wherein at least a portion of one of the films is impervious. The dam includes a set of fibers located between the first film and the second film, such fibers being spaced apart a distance generally equal to the average mesial-distal width of a tooth. At least one of the films is gathered along the length of the fibers.

BRIEF DESCRIPTION OF THE DRAWINGS

FIG. 1 is a fragmentary plan view of a dental isolation dam in accordance with one embodiment of the invention;

FIG. 2 is an enlarged, schematic cross-sectional view taken generally along lines 2—2 of FIG. 1;

FIG. 3 is a plan view of a lower jaw showing one example of use of the dental dam of FIGS. 1 and 2 with its crisscrossed fibers fitted around isolated teeth;

DETAILED DESCRIPTION OF THE PREFERRED EMBODIMENTS

Figure 4:
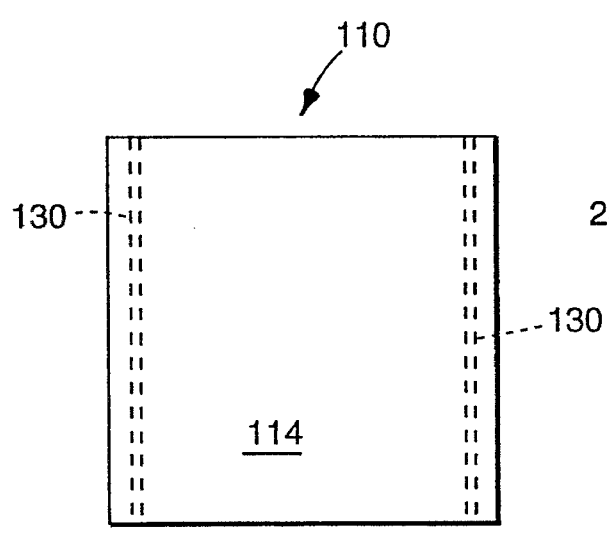
FIG. 4 is a plan view of a dam according to another embodiment of the invention, wherein the dam has a deformable metal wire extending along two opposing sides of the dam to hold the dam in a desired shape.

As used herein, the term "elastic" means a natural or synthetic polymer which at room temperature can be repeatedly stretched to at least two times (e.g., 100% elongation) its original relaxed length and which, after removal of the tensile stress, will forcibly return to approximately its original relaxed length. The term "impervious" means impermeable under normal room temperature and pressure conditions to the passage of fluids and microorganisms.

A dental isolation dam 10 is shown in FIGS. 1–2 and comprises a laminate that includes a first ply 11 and a second ply 13. First ply 11 includes a first set of generally parallel elastic fibers 12 sandwiched between an impervious first film 14 and an impervious second film 16. Second ply 13 is somewhat similar to first ply 11, and has a second set of generally parallel elastic fibers 18 sandwiched between an impervious third film 15 and an impervious fourth film 17. Fibers 12, 18 extend completely across dam 10.

To make the first ply 11, fibers 12 are stretched to several times their relaxed length as the films 14, 16 are heat-sealed together. Optionally, both fibers 12 and films 14, 16 are stretched during the heat sealing process. After the first ply 11 is sealed together, fibers 12 are allowed to return to a relaxed length, resulting in a shirred laminate that has a puckered or gathered configuration. The second ply 13 is made in the same manner.

First ply 11 is assembled to the second ply 13 in such a manner that the first set of fibers 12 is arranged in a direction perpendicular to the second set of fibers 18 to provide a crisscrossed, rectangular pattern. During assembly, ply 11 is slightly stretched in a direction along the length of fibers 12 and ply 13 is slightly stretched in a direction along the length of fibers 18; plies 11, 13 are then heat-sealed to each other while in their slightly stretched shape.

Fibers 12 are spaced apart about the average mesial-distal width of a tooth, preferably between about 5 mm and 11.5 mm, and more preferably between about 6 mm and 10 mm. Fibers 18 are spaced apart about the average buccal-lingual width of a tooth, preferably between about 6 mm and 12 mm, and more preferably between about 7 mm and 11 mm. The rectangular orientation of fibers 12, 18 enables the practitioner to rotate dam 10 as needed to accommodate various tooth sizes.

A plan view of dam 10 is shown in FIG. 1, wherein fibers 12, 18 are depicted in dashed lines. FIG. 2 is a cross-sectional view of dam 10 in schematic form, wherein films 14–17 are shown for instructional purposes in a laminate but not heat sealed together. As an option, films 15, 16 could be deleted, and fibers 12, 18 (if made of thermoplastic material) could then be fused together at their points of intersection as film 14 is heat-sealed to film 17.

Fibers 12, 18 can be made of natural or synthetic materials. The fibers 12, 18 may comprise one or more strands (if more than one strand is used, the fiber is commonly referred to as a yarn). Suitable fibers have a denier between about 400 and 5,000 and include spandex, natural or synthetic rubber, linear block copolymers, and throsted elastomers (for example, an elastomeric strand that is spirally wrapped about its exterior with a yarn or nonwoven web). A particularly preferred fiber is spandex and has a denier of about 2240. Before the fibers 12, 18 are attached between the films 14, 16 and film 15, 17 respectively, fibers 12, 18 can be stretched at least to a length that is in the range between about 2 and 8 times their relaxed length and preferably to at least a length that is in the range between about 2 and 4 times their relaxed length.

Films 14–17 can be homopolymers, copolymers, blends, coextrusions or multi-layer constructions with polymers that soften at higher temperatures. Films 14–17 are preferably made of polymers such as polyurethanes, elastomeric polyesters, natural or synthetic rubbers, ethylene:vinyl acetate copolymers, ethyl-acrylate:methacrylate copolymers, ionomers (e.g., SURLYN), linear low density polyethylene and combinations thereof. Polyurethanes are presently preferred.

It is also presently preferred that at least one of films 14–17 be non-transparent or colored by pigments or dyes to facilitate locating the punched holes over the designated teeth and facilitate positioning the dam 10 in the limited and visually restrictive working space in the mouth.

Films 14–17 can be laminated to themselves or other homopolymeric films (e.g., polyethylene or polypropylene). Alternatively, one or more of the films 14–17 can be nonwoven webs made of polypropylene, rayon or polyester fibers, blown microfiber constructions, thermobonded, spunbonded or spunlaced constructions or traditional woven or knit fabrics.

Suitable films each have a thickness of about 0.5 to about 10 mils and preferably can be stretched at least to a length in the range between about one-fourth to about 4 times their relaxed length. Preferred films each have a thickness of about 0.5 to about 2 mils and can be stretched at least to a length in the range between about 3 to about 4 times their relaxed length. The thickness of each of the plies 11, 13 in regions where the fibers 12, 18 are not present is preferably about 1.0 to about 20 mils and more preferably about 1.5 to about 4 mils.

Both the fibers 12, 18 and the films 14–17 should be non-toxic, free of objectionable taste and odor, and suitable for use in the mouth. The laminate should have sufficient strength to avoid rupture or tearing during normal placement and use and should be free of pin holes and the like which might otherwise enable the seepage of moisture and result in the passage of microorganisms through the dam.

Optionally, conventional adjuvants such as lubricants, plasticizers, stabilizers, diluents, binders, extending or reinforcing fillers (such as fumed silica or zinc oxide), flavorants, medicaments (e.g., bactericidal agents and/or fungicidal agents), process aids and other ingredients that will be apparent to those skilled in the art may be added to the films 14–17 or fibers 12, 18 as desired.

In preparation for placement of dam 10 in the mouth of a patient, the position of one or more teeth to be isolated is marked on dam 10 between fibers 12, 18. Using a dam punch, one or more holes are punched in dam 10 corresponding to the marked position(s). An example of the use of dam 10 is illustrated in FIG. 3, wherein three holes have been punched in dam 10 and the holes have been placed over teeth $T_1$–$T_3$. With dam 10 somewhat stretched over teeth $T_1$–$T_3$, the fibers 12, 18 that are next to the punched holes are placed about the occlusal portions of teeth $T_1$–$T_3$ and moved gingivally toward the necks of teeth $T_1$–$T_3$ such that one of the fibers 12 is on the mesial side of $T_1$, the next adjacent fiber is placed interproximally between teeth $T_1$,$T_2$, the next adjacent fiber 12 is placed interproximally between teeth $T_2$,$T_3$ and the next adjacent fiber 12 is placed on the distal side of $T_3$; in addition, an adjacent pair of fibers 18 perpendicular to fibers 12 is located along the lingual and buccal sides of teeth $T_1$–$T_3$. As each tooth $T_1$–$T_3$ is extended through the perforation, that portion of the dam 10 is then released and allowed to return to its normal unstretched configuration with the previously identified fibers 12, 18 snugly fitting around the necks of exposed tooth.

Dam 10 is then stretched over frame 20. Frame 20 is known in the dental art as a Young frame and comprises opposed legs 22, 24 connected by a curved intermediate leg 26 that fits about the patient's jaw. Frame 20 has a plurality of blunt-ended extensions 28 that are used to fasten the stretched dam 10 to keep it taut. Optionally, clips may be used on the buccal and lingual sides of one or more of teeth $T_1$–$T_3$ to grip adjacent pairs of fibers 12 and thereby tighten the grip of the fibers 12 on the chosen tooth or teeth. If desired, a retainer clamp (not shown) conventionally known in the art can be used on tooth $T_3$ to assist in maintaining the dam 10 in position.

Another embodiment of the invention is shown in FIG. 4, wherein dam 110 includes a two-ply fiber and film laminate essentially identical to the laminate described in connection with dam 10 shown in FIGS. 1–3 and also includes two deformable flat metal strips or wires 130 extending along the periphery of opposing sides of dam 110. When bent by hand, wires 130 readily deform past their yield point and take on the desired configuration. Wires 130 are preferably heat sealed between film 114 and a second, adjacent film (not shown). Wires 130 maintain dam 110 taut and are bent to conform to the configuration of the patient's face in the area about the mouth. Wires 130 facilitate use of the dam 110 without using a frame such as frame 20 shown in FIG. 3. Optionally, dam 110 is sized to fit inside the mouth of the patient. Wires 130 also facilitate insertion of dam 110 in the mouth of a patient. Wires 130 help the dam 110 maintain a generally U-shaped configuration matching the angle between the jaws of the open mouth and help the dam 110 to avoid collapsing upon itself. As an alternative to the dam 110 shown in FIG. 4, one or more wires similar to wires 130 could extend around the entire periphery of the dam, and the dam could optionally have an oval shape.

Figure 5:
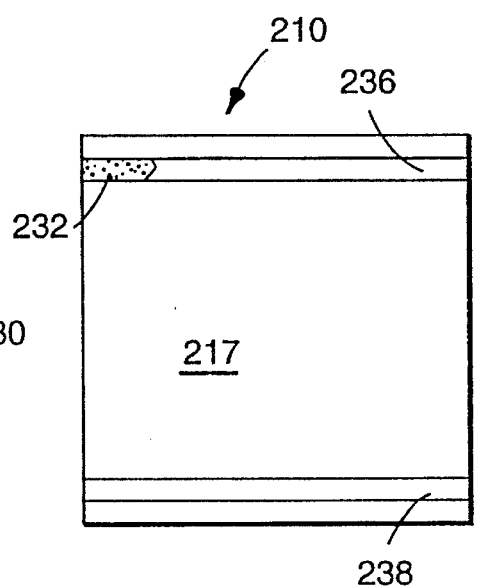
FIG. 5 is a plan view of a dam according to another embodiment, wherein strips of adhesive are connected to the periphery of the dam.

FIG. 5 depicts another embodiment of the invention, wherein dam 210 includes a two-ply fiber and film laminate essentially identical to the laminate of dam 10 in FIGS. 1–3, and further comprises upper and lower adhesive strips 232 (only one shown) connected to dam 210. Strips 232 are attached to the outer surface of film 217 of dam 210 and are covered with upper release liner or protective sheet 236 and lower release liner or protective sheet 238. After dam 210 is placed about the teeth to be isolated, sheet 236 is removed from strip 232 and that portion of dam 210 is somewhat stretched and adhered to the face of the patient in the area above the upper lip and below the nose. Then sheet 238 is removed from the lower strip and that portion of dam 210 is somewhat stretched and adhered to the patient's face below the isolated teeth and under the chin. Preferably strips 232 are positioned as shown in FIG. 5 on opposing sides of dam 210 near the periphery and extend substantially the entire length of dam 210. Optionally, adhesive strips may instead extend along the other two sides of dam 210, or extend along all four sides of the dam 210. If desired, all or some of the strips may be discontinuous or interrupted by non-adhesive coated areas.

Adhesive strips 232 are made using any suitable double coated tape that adheres well to both the laminate and the patient's skin. Preferably, adhesive strips 232 are made of a double coated medical tape (3M; No. 1522) which consists of a polyethylene film coated on both sides with a biocompatible pressure sensitive skin adhesive such as an acrylate adhesive. This adhesive is particularly preferred because it provides a relatively high level of adhesion to mammalian facial skin which in several species has a high concentration of glands secreting oils that can disrupt continuous adhesion of the tape. Protective sheets 236, 238 are preferably made of a silicone coated paper.

Figure 6:
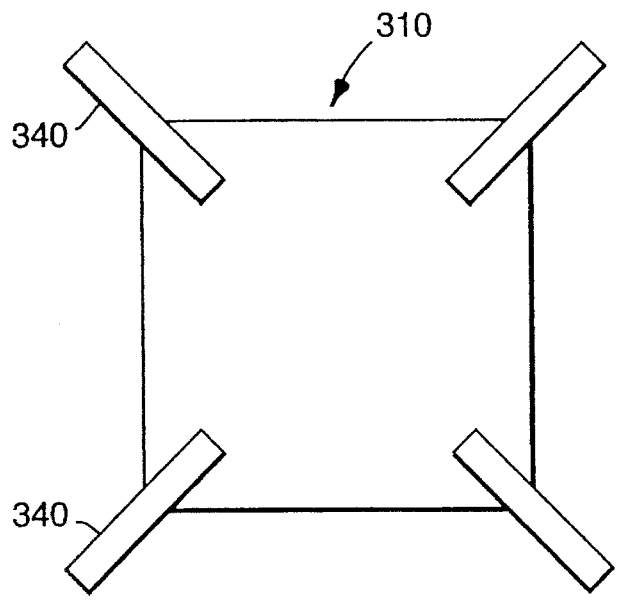
FIG. 6 is a plan view of another embodiment of the invention, wherein adhesive tabs extend diagonally outwardly from the corners of the dam.

Another embodiment of the invention is illustrated in FIG. 6, wherein dam 310 includes a two-ply fiber and film laminate identical to the laminate of dam 10 shown in FIGS. 1–3, and further includes four spaced-apart adhesive tabs 340 that extend outwardly in a diagonal direction from a central region of dam 310 and from the respective four corners of dam 310. After dam 310 is placed about the teeth to be isolated, release liners are removed from both of the upper tabs 340 and the upper portion of dam 310 is somewhat stretched and adhered to the face of the patient in the area of the cheeks. Then release liners are removed from both of the lower tabs 340 and the lower portion of dam 310 is somewhat stretched and adhered to the patient's face under the chin.

Adhesive tabs 340 are preferably made of the same materials used to make adhesive strips 232, except that the tabs are made of a single coated medical tape (3M; No. 1525L). Release liners are made of materials similar to those used to make protective sheets 236, 238. Optionally, the tabs 340 are packaged as initially separate from the laminate of dam 310, to enable the dentist to place the tabs 340 in the most appropriate orientations in accordance with particular facial features of the patient or the position of the tooth to be isolated; in such instances, each release liner is pre-cut into two portions so that one portion of the tab adhesive remains covered as the other portion is applied where desired to the laminate by the dentist.

Figure 7:
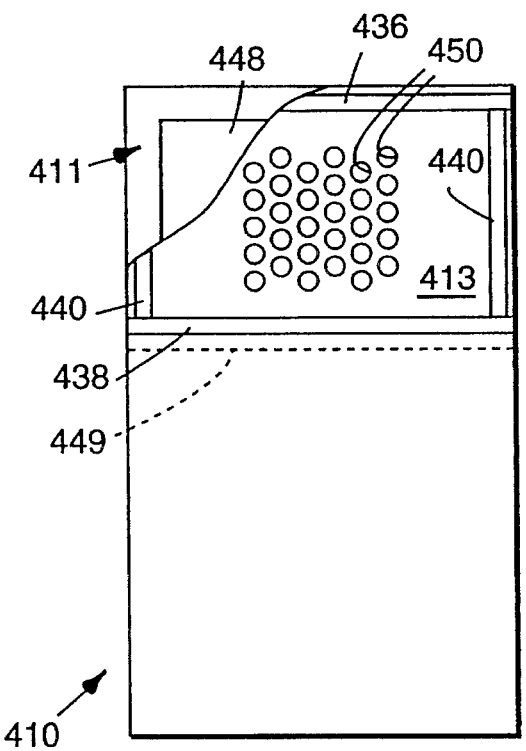
FIG. 7 is a plan view of yet another embodiment of the invention, wherein a portion of filtration material is connected to the dam for covering the nose of a patient.

FIG. 7 depicts another embodiment of the invention, wherein filtration material 448 is connected to dam 410 for covering the nose of a patient and protecting the patient from inhalation of contaminants that may become air-borne during a dental procedure. Dam 410 includes a two-ply fiber and film laminate essentially identical to the laminate of dam 10 depicted in FIGS. 1–3, and additionally includes a section of filtration material 448 that is located between plies 411, 413 in an upper portion of dam 410 above the dashed line designated 449 in FIG. 7. Filtration material 448 is preferably located in a pocket made by heat-sealing the plies 411, 413 together to form a rectangular border surrounding the filtration material 448 in the upper portion of dam 410; as a consequence, the filtration material 448 and plies 411, 413 lie in planes generally parallel to one another. The films of the plies 411, 413 in the upper portion of the dam 410 which is to be positioned over the nostrils of the patient contain a plurality of perforations 450 for passage of air therethrough.

Filtration material 448 is made of web or webs of the type used to fabricate disposable face masks for use in the medical and dental industries. Filtration material 448 is a fibrous web, and preferably comprises an electrically charged melt-blown polypropylene microfiber web. Webs of other melt-blown fibers are also suitable, such as taught in Wente, Van A., "Superfine Thermoplastic Fibers" in *Industrial Engineering Chemistry*, Vol. 48, pp. 1342 et seq. (1956), especially when in a persistent electrically charged form such as described in U.S. Pat. No. 4,215,682. Preferably the fibers of filtration material 448 have an average diameter of less than about 10 micrometers. Alternative fibrous webs may be made of rosin-wool, glass fiber or electrically charged fibrillated-films such as taught in U.S. Pat. RE. No. 31,285.

Optionally, filtration material 448 may be made of a triple layer construction as is well known to those skilled in the filtration art. The triple layer construction comprises a filtration layer sandwiched between an inner and an outer shaping layer. As with molded face masks, the filtration material 448 may have a pliable band (not shown) made of aluminum adhesively connected to one side of the filtration material 448 or the plies 411, 413 to complementally conform to the shape of the patient's face adjacent the bridge of the nose.

Adhesive strips made of double coated tape similar to adhesive strips 232 illustrated in FIG. 5 are located on ply 413 along a rectangular-shaped path overlying the heat-sealed border surrounding the filtration material 448. The strips are protected by top, bottom and side sheets 436, 438 and 440, respectively. Sheets 436, 438, 440 are essentially identical in composition to sheets 236, 238 depicted in FIG. 5. Sheets 440 and underlying strips extend from the outer ends of sheets 436, 438 and corresponding underlying strips.

After dam 410 is placed about the teeth to be isolated, sheet 436 is removed from its adhesive strip and adjacent portions of filtration material 448 are adhered to the face of the patient in the area next to the bridge of the nose. Sheet 438 is then removed from its adhesive strip and adjacent portions of filtration material 448 are adhered to that portion of the patient's face below the nose and above the upper lip. Next, sheets 440 are removed and the exposed adhesive strips are adhered to the patient's cheeks. The remainder of dam 410 is held taut and in position using other means (not shown in FIG. 7) such as the adhesive strips that are shown in FIG. 5, the adhesive tabs 340 as depicted in FIG. 6 or with a frame similar to frame 20 illustrated in FIG. 3.

The dental isolation dam of the invention can be easily placed by the practitioner. The elastic fibers tend to aid in guiding the punched holes over the selected tooth or teeth and, when released, clinch the periphery of the neck of the isolated tooth or teeth. Advantageously, dental floss or other types of separate cords are not necessary to place the dam over the tooth or to hold the dam in position. Moreover, the gathered laminate and parallel and crisscrossed fibers provide texture for the dam and make it less likely to cling to mucosal tissue than a smooth rubber dam. This may enhance patient comfort by enabling the patient to breathe more easily.

With the incorporation of adhesive strips or tabs, the isolation dam of the invention offers both ease of placement and flexibility of use for the practitioner. The dam can be easily utilized for various dental procedures regardless of the mode of operation of the practitioner. Not only is there no longer a need in many instances to purchase or sterilize hardware such as frames or retainer clamps, but also there is often less obstruction of the limited working space in and about the patient's mouth.

The present invention will be further understood in view of the following examples which are merely illustrative and not meant to limit the scope of the invention.

EXAMPLE 1

Two 0.85 mil thick polyurethane films were prepared using the procedure described in Example 1, lines 13–26 of U.S. Pat. No. 4,499,896. The releasable layer was removed from each film as it was fed from above and below between two smooth steel nip rolls of a calendar. Both nip rolls were heated to 116° C. and squeezed together at a pressure of 1.1 kg/cm$^2$. Lycra XA 700 denier (275 micrometer diameter) spandex fibers (E. I. dupont de Nemours & Co., Wilmington, Del.) spaced 6.4 mm apart and stretched about three times their original relaxed length were fed between the polyurethane films into the heated nip rolls. The fibers and films were heat sealed together at 1.5 meters per minute into a single ply that, after passing through the rolls, immediately puckered.

A 15 cm square sample was cut from the single ply. Eight holes corresponding to the position of teeth in one quadrant of the mouth were punched between the fibers with a rubber dam punch (Henry Schein Inc., Port Washington, N.Y.; No. 100-8148). The sample was stretched over the teeth with the fiber being used similar to the use of dental floss to carry the sample through the interproximal areas between the teeth. The elasticity of the fibers and the films enabled the sample to snugly fit around the necks of the designated teeth to form a seal.

EXAMPLE 2

A single ply is prepared following the procedure of EXAMPLE 1, except that Lycra XA 2240 denier (500 micrometer diameter) spandex fibers (E. I. dupont de Nemours & Co.) are used instead of Lycra XA 700 denier spandex fibers. After the fibers are positioned interproximally between the teeth, the dam is stretched for final placement on a frame. Such larger diameter fibers should exhibit less of a tendency to dislodge from between the teeth than the smaller diameter fibers described in Example 1.

EXAMPLE 3

A first 15 cm square ply of EXAMPLE 2 is hand stretched in a direction parallel to the direction of the fibers to about two times its relaxed length. A second 15 cm square ply of EXAMPLE 2 is hand stretched in a direction parallel to the direction of the fibers to about two times its relaxed length. The stretched second ply is held atop the stretched first ply with the fibers of the second ply oriented perpendicular to the fibers of the first ply. The first ply-second ply laminate is placed between two silicone release liners and pressed between platens of a Sentinel press (Model# 808; Sentinel Packaging Industries, Hyannis, Mass). The platens are preheated to about 150° C. The laminate is maintained in the press for about 3 seconds at a line pressure of 4.2 kg/cm$^3$. The laminate is then removed from the press and held by hand in the stretched orientation until it cools (about 2–3 seconds). The release liners are removed from the laminate and the laminate is allowed to return to a relaxed state. The laminate immediately puckers and exhibits a crisscrossed fiber configuration which, when placed about the teeth, should snugly clinch around the necks of the designated teeth.

We claim:

1. A dental isolation dam comprising:
   a first film;
   a second film, at least a portion of one of said films being impervious to the passage of fluids and microorganisms under normal room temperature and pressure conditions; and
   a first set of fibers located between said first film and said second film, at least certain fibers of said first set being arranged in adjacent pairs and spaced apart a distance generally equal to the average mesial-distal width of a tooth.

2. The dam of claim 1, wherein at least one of said films is gathered along the length of said fibers.

3. The dam of claim 1, wherein said first film and said second film can be stretched to a length between about one-fourth and 4 times their relaxed length.

4. The dam of claim 1, wherein said fibers can be stretched to a length between about 2 and 8 times their relaxed length.

5. The dam of claim 1, further comprising an adhesive connected to said first film.

6. The dam of claim 5, further comprising one or more tabs connected to said first film and extending outwardly past said first film and said second film in a direction away from a central region of said dam, said adhesive being located on an outer portion of said tabs.

7. The dam of claim 6, wherein said first film and said second film have an overall generally rectangular configuration, whereby said tabs extend outwardly in a diagonal direction relative to said first film and said second film.

8. The dam of claim 1, further comprising a deformable wire connected to one of said films for shaping the dam to conform to the configuration of a patient's face.

9. The dam of claim 1, wherein said first film and said second film comprise polyurethane.

10. The dam of claim 1, wherein said fibers comprise spandex.

11. The dam of claim 1, wherein said dam has an overall configuration to substantially fit within the entire confines of the oral cavity.

12. The dam of claim 1, wherein said first set of fibers extend in generally parallel directions, and further comprising a second set of fibers extending in generally parallel directions generally transverse to the directions of extension of said first set, at least certain fibers of said second set being arranged in adjacent pairs and spaced apart a distance generally equal to the average buccal-lingual width of a tooth.

13. The dam of claim 12, wherein said first set are spaced apart about 6 mm to about 10 mm and said second set are spaced apart about 7 mm to about 11 mm.

14. The dam of claim 12, further comprising an adhesive connected to said first film.

15. The dam of claim 14, further comprising one or more tabs connected to said first film and extending outwardly past said first film and said second film in a direction away from a central region of said dam, said adhesive being located on an outer portion of said tabs.

16. The dam of claim 15, wherein said first film and said second film have an overall generally rectangular configuration, whereby said tabs extend outwardly in a diagonal direction relative to said first film and said second film.

17. The dam of claim 12, further comprising a deformable wire connected to one of said films for shaping the dam to conform to the configuration of a patient's face.

18. The dam of claim 12, wherein at least one of said films is gathered along the length of said fibers.

19. The dam of claim 1, further comprising a mask portion connected to one of said films, said mask portion including a section of filtration material for covering the nose.

20. A dental procedure comprising the steps of:
    placing a dental dam over at least a portion of the oral cavity of a patient;
    moving the dam to cause at least one tooth to project through a hole in the dam; and
    adhesively connecting a portion of the dam to the face of the patient to facilitate retaining the dam in place, wherein said step of adhesively connecting a portion of the dam to the face of the patient includes the step of applying an adhesive to at least one region of the patient's face below said at least one tooth.

21. The dental procedure of claim 20, wherein the step of moving the dam to cause at least one tooth to project through a hole in the dam includes the step of moving at least one elastic fiber of the dam along the side of the tooth.

22. The dental procedure of claim 20, wherein said step of adhesively connecting a portion of the dam to the patient includes the step of contacting the patient with one or more adhesive-bearing tabs that extend outwardly from a central region of the dam.

23. The dental procedure of claim 20, including the step of placing a section of filtration material of the dam over the nasal passages of the patient.

24. A dental isolation dam comprising:
    a film, at least a portion of said film being impervious to the passage of fluids and microorganisms under normal room temperature and pressure conditions; and
    a mask portion connected to said film, said mask portion including a section of filtration material for covering the nose and enabling passage of air therethrough, wherein said film and said section of filtration material lie in planes generally parallel to one another and wherein said passage of air is generally perpendicular to said film and said section of filtration material; and
    a first set of fibers extending in generally parallel directions, at least certain fibers of said first set being arranged in adjacent pairs and spaced apart a distance equal to the average mesial-distal width of a tooth.

25. The dam of claim 24, further comprising an adhesive connected to said film.

26. The dam of claim 24, further comprising a second set of fibers extending in generally parallel directions, and wherein said first set and said second set are arranged in a crisscrossed configuration, the fibers of said first set being spaced apart about 6 mm to about 10 mm and the fibers of said second set being spaced apart about 7 mm to 11 mm.

27. The dam of claim 24, wherein said section of filtration material comprises a fibrous web.

28. The dam of claim 24 including an adhesive connected to the film for releasably adhering the dam to the face of a patient.

29. The dam of claim 28, wherein at least a portion of said adhesive is next to said filtration material.

30. The dam of claim 24, further comprising a deformable wire connected to said film for shaping the dam to conform to the configuration of a patient's face.

31. A dental isolation dam comprising:
    a film, at least a portion of said film being impervious to the passage of fluids and microorganisms under normal room temperature and pressure conditions;
    a first set of fibers extending across said film, said first set of fibers including at least two fibers that extend in generally parallel directions and are spaced apart a distance equal to the average mesial-distal width of a tooth, and
    a mask portion connected to said film, said mask portion including a section of filtration material for covering the nose and enabling passage of air therethrough, wherein said film and said section of filtration material lie in planes generally parallel to one another and wherein said passage of air is generally perpendicular to said film and said section of filtration material, wherein said section of filtration material comprises a fibrous web, and wherein said fibrous web comprises electrically charged melt-blown polypropylene microfibers.

32. A dental isolation dam comprising:
    a first film;
    a second film, at least a portion of one of said films being impervious to the passage of fluids and microorganisms under normal room temperature and pressure conditions; and a set of fibers located between said first film and said second film and spaced apart a distance generally equal to the average mesial-distal width of a tooth, at least one of said films being gathered along the length of said fibers.

33. The dam of claim 32, wherein said fibers extend in generally parallel directions relative to each other.

34. The dam of claim 32, further comprising an adhesive connected to said first film.

35. The dam of claim 34, further comprising one or more tabs connected to said first film and extending outwardly past said first film and said second film in a direction away from a central region of said dam, said adhesive being located on an outer portion of said tabs.

36. The dam of claim 32, further comprising a deformable wire connected to one of said films for shaping the dam to conform to the configuration of a patient's face.

37. The dam of claim 32, further comprising a mask portion connected to one of said films, said mask portion including a section of filtration material for covering the nose.

* * * * *